United States Patent
Beling et al.

(10) Patent No.: US 7,931,622 B2
(45) Date of Patent: Apr. 26, 2011

(54) TIP PROTECTOR FOR CANNULA, TROCAR AND/OR CANNULA TROCAR COMBINATION

(75) Inventors: William Beling, New Brighton, MN (US); Ronald Travis, Spring Lake Park, MN (US); Kristin Finberg, Minneapolis, MN (US); James Marrs, Arden Hills, MN (US); Lyle V. Peterson, Maple Grove, MN (US); Randall Cronquist, Vadnais Heights, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 74 days.

(21) Appl. No.: 12/076,495

(22) Filed: Mar. 19, 2008

(65) Prior Publication Data

US 2009/0240203 A1    Sep. 24, 2009

(51) Int. Cl.
    *A61M 5/178* (2006.01)
(52) U.S. Cl. .............. 604/164.08; 604/164.07
(58) Field of Classification Search ............ 604/164.07, 604/164.08, 192
    See application file for complete search history.

(56) References Cited

U.S. PATENT DOCUMENTS

| | | | |
|---|---|---|---|
| 5,591,133 A | 1/1997 | Feuerborn et al. | |
| 5,766,220 A | 6/1998 | Moenning | |
| 5,968,016 A | 10/1999 | Yerfino et al. | |
| 6,254,575 B1 * | 7/2001 | Thorne et al. | 604/198 |
| 6,663,605 B2 | 12/2003 | Chan | |
| 6,837,874 B1 * | 1/2005 | Popov | 604/164.06 |
| 7,303,548 B2 | 12/2007 | Rhad et al. | |
| 2003/0060769 A1 * | 3/2003 | Rhad et al. | 604/164.07 |
| 2005/0187520 A1 | 8/2005 | Gammons | |
| 2007/0129686 A1 * | 6/2007 | Daily et al. | 604/192 |

* cited by examiner

*Primary Examiner* — Nicholas D Lucchesi
*Assistant Examiner* — Gerald Landry, II
(74) *Attorney, Agent, or Firm* — Louis Woo

(57) ABSTRACT

A needle protector that protects the tip or distal end of a cannula, a trocar, or a cannula/trocar combination, is provided by an extruded tubing that has at least a section thereof that includes one or a plurality of protrusions or protuberances that are configured in a given fashion so that there is a slight bend created at that section of the tube, when the tube is fitted onto a cannula or trocar with the protrusions coming into contact with the outer diameter surface of the cannula or trocar. This results in friction contact between the protrusions and the cannula or trocar to maintain the tube protector in place relative to the cannula or trocar. The protrusions may be punched or lanced in the tube to a given depth towards the interior of the tube to establish a given friction contact.

14 Claims, 5 Drawing Sheets ized by punching deeper into the tube protector to thereby extend the tips of the protrusions further into the interior of the tube protector. And insofar as the tips of the protrusions are the contact points or surfaces between the tube protector and the cannula, any variation of the ID of the tube protector due to manufacturing tolerances does not come into play.

TIP PROTECTOR FOR CANNULA, TROCAR AND/OR CANNULA TROCAR COMBINATION

FIELD OF THE INVENTION

The present invention relates to cannulas and/or trocars, and more particularly relates to a tube protector for a cannula, a trocar, and/or a cannula that has fitted thereinto a trocar.

BACKGROUND OF THE INVENTION

In the manufacture, distribution and use of needle products, it is important to protect the tip or distal end of the needle, cannula or trocar from damage. There are many ways to accomplish this. One typical method is to use an extruded tube cut to the appropriate length with the inside diameter (ID) of the tube sized to provide a friction fit to the outside diameter (OD) of the needle, trocar or the cannula that the tube is to protect. It is reasonable to assume a tolerance of +/−0.002 for the ID of the extruded tubing.

To design a frictional fit between the tip protector and the trocar or cannula so that the tip protector does not fall off or be removed too easily from the cannula or trocar (cannula/trocar), the design of the tube protector is such that the ID of the tube protector would be substantially the same as the OD of the cannula/trocar, so that there is a line-to-line friction fit between the tube protector and the cannula/trocar in the loosest condition. But the tolerances for the manufacture of the cannula or trocar, as well as for the manufacture of the tube protector may vary. For example, the tolerance for the manufacturing of a stainless steel cannula or trocar could be controlled better than that for the manufacturing of a plastic tube protector. Thus, a stainless steel trocar or cannula could be assumed to be able to be manufactured with a constant OD, while a plastic tube protector could not be so assumed. Accordingly, in the case where the OD of the cannula or trocar is assumed to be constant, it may well be the ID of the tube protector could vary to such an extent that it is tighter than a line-to-line friction fit, so that there is quite a bit of friction interference between the tube and the cannula/trocar, therefore making it difficult to remove the tube from the cannula/trocar.

In most applications, the removal of the tube protector is accomplished by holding the hub of the cannula or trocar and simply pulling the tube protector pass the tip of the cannula/trocar for disposal. The frictional force between the tube protector and the cannula/trocar is therefore also dependent on the strength of the user. On the other hand, if the tube were manufactured to have an ID greater than the OD of the cannula/trocar so that the tube is too loose relative to the cannula/trocar, the tube protector would simply fall off when fitted about the cannula/trocar.

The importance of the friction fit between a tube protector and a cannula is amplified when a trocar is fitted into a cannula, with the cannula being separable from the trocar. An example of such combination cannula/trocar is described in U.S. publication 2007/0149921, and its companion publication 2007/0149920, both assigned to the assignee of the instant invention. In those publications, it is disclosed that an infusion site has a cannula extending from its bottom surface, and a trocar or needle extending through the cannula having its tip extending beyond the distal end of the infusion site cannula. The combined cannula/trocar is used for insertion into the patient so that the cannula may establish a fluid communications path between the infusion site and a portal reservoir implanted in the patient. The trocar is removed after the cannula makes connection with the reservoir.

For such combined cannula/trocar device, the cannula as well as the trocar, particularly the trocar tip extending from the distal end of the cannula, need to be protected, for example by a tube protector mentioned above. But given the acceptable manufacture tolerance of a tube protector, there may well be instances where the friction contact between the ID of the tube protector and the OD of the cannula are such that when a user tries to remove the tube protector from the cannula, the static friction and/or vacuum suction created by the friction fit between the tube protector and the cannula would instead cause the cannula to be moved in unison or tandem with the tube protector, so that the cannula is separated from the trocar. This happens because the force required to overcome the friction fit between the tube protector and the cannula is greater than that required to overcome the friction fit between the cannula (its ID) and the trocar (its OD). Therefore, instead of removing the tube protector so that the cannula can be used with the trocar, the cannula is removed from the trocar along with the tube protector, thereby leaving the combination cannula/trocar device not usable.

SUMMARY OF THE PRESENT INVENTION

To ensure that the removal of the tube protector from a cannula in a combination cannula/trocar device does not cause the cannula to be removed from the trocar, the present invention tube protector minimizes the static friction between the tube protector and the cannula by having an inside diameter that is sufficiently greater than the outside diameter of the cannula so that the tube protector is freely movable along the cannula when it is fitted thereabout. To prevent the tube protector from freely falling off the cannula, a plurality of protrusions, protuberances or dimples, are formed on the tube protector with the protrusions, or more precisely the tips or distal ends of the protrusions, in contact with the outer diameter surface of the cannula.

The making or manufacturing of the protrusions in the tube protector may be controlled with better tolerance than the manufacturing of the tube protector itself. And given that the protrusions are in contact with the cannula, and that the protrusions cause the tube protector to bend at a slight angle relative to the straight cannula, an effective friction contact is established between the tube protector and the cannula so that the tube protector would not freely fall off the cannula. Further, the force required to remove the tube protector from the cannula due to the friction contact between the protrusions and the outer surface of the cannula is less than the force required to overcome the friction contact between the inner surface of the cannula and the outer surface of the trocar, as the cannula and the trocar are in line-to-line contact.

To effect an effective friction contact between the tube protector and the cannula, it was found that a plurality of protrusions—for example three protrusions, protuberances or dimples—may be provided onto the tube protector to extend inwardly into the interior of the tube protector. These protrusions may be effected by punching or lancing the tube protector, with one of the protrusions being produced 180° opposed to and directly across from the other two protrusions, which may be in alignment along the length of the tube but positioned above and below the one opposed protrusion.

By having this "three dimple" arrangement, a slight bend is created for the tube protector as the tube protector fits onto the cannula. This bend, along with the protrusions at the inner diameter surface of the tube protector, provides a friction contact or fit that is readily adjustable, for example by adjusting the depth(s) of the punch(es) used to produce the protrusions. This protrusion friction contact arrangement was found also to provide robust retention of the tube to the cannula during other parts of the manufacture processes, such as for example the sterilization process, before the tube protector needs to be removed from the cannula prior to use. It has further been found that the force required to remove the tube protector from the cannula is approximately 1/10 the force required to remove the cannula from the trocar, for example approximately 0.25 lb. force for the former compared to 2.25 lb. force for the latter.

Although a "three dimple" protrusions arrangement is disclosed, a smaller number of protrusions, for example one, or a number greater than three protrusions may also be used.

The instant invention therefore relates to a protector for a cannula that comprises an elongate tube having a length to enable the protector to fit about the cannula, and extend from the base of the cannula to beyond the tip of the cannula. The tube has an inner diameter surface not in contact with the outer diameter surface of the cannula when fitted about the cannula. The tube further includes at least one protrusion extending inwards towards its center, with the protrusion being dimensioned to come into contact with the outer diameter surface of the cannula when the tube is fitted about the cannula, so that the tube is held in place relative to the cannula by friction contact between the protrusion and the outer diameter surface of the cannula.

The present invention also relates to a combination that includes an infusion site having a base with a bottom surface and a cannula having a distal end extending from the bottom surface, a trocar having an outer diameter surface and a tip extending through the base into the cannula with its tip extending beyond the distal end of the cannula, and a tube having a distal end and a proximal end fitted about the cannula with the distal end of the tube extending beyond the tip of the trocar when the proximal end of the tube is in substantial abutment with the bottom surface of the base to prevent the tip of the trocar from being exposed. The cannula is held to the trocar by friction contact between the inner diameter surface of the cannula and the outer diameter surface of the trocar. The tube has an inner diameter that is sufficiently greater than the outer diameter of the cannula such that the tube would be freely movable relative to the cannula when fitted about the cannula. The tube further includes at least one protrusion extending inwardly towards its interior that comes into contact with the outer diameter surface of the cannula to establish friction contact between the protrusion and the cannula when the tube is fitted about the cannula, such that the tube is prevented from being separated from the cannula without a predetermined force being exerted to remove the tube from the cannula.

The present invention is further directed to a protector for a cannula that has a distal end and a trocar fitted therethrough, the trocar having a tip that extends beyond the distal end of the cannula. The cannula and the trocar are in friction contact with each other along their respective outer diameter surface and inner diameter surface. The protector comprises a tube having a length longer than either of the trocar and the cannula so that the tip of the trocar and the distal end of the cannula are covered by the distal end of the tube when the tube is fully fitted over the cannula. The tube has a diameter greater than the diameter of the cannula so that the tube is freely movable relative to the cannula when fitted about the cannula. The tube further has at least one protrusion extending inwardly towards its interior to be in contact with the outer wall of the cannula when the tube is fitted about the cannula to establish friction contact between the protrusion and the cannula so that a predetermined force is required to be applied to the tube in order to remove the tube from the cannula.

The invention further is directed to a method for making a protector for a cannula. The method includes the step of extruding a tube that has a diameter that is larger than the diameter of the cannula so that the tube is freely movable along the cannula if the tube is fitted about the cannula. The method further includes the step of effecting at least one protrusion in the tube with the protrusion extending into the interior of the tube and being in friction contact with the outer surface of the cannula when the tube is fitted about the cannula so that the tube is removable from the cannula only if a predetermined force is exerted to remove the tube from the cannula.

BRIEF DESCRIPTION OF THE FIGURES

The present invention will become apparent and the invention itself will be best understood with reference to the following description taken in conjunction with the accompanying drawings, wherein.

DETAILED DESCRIPTION OF THE INVENTION

Figure 1B:
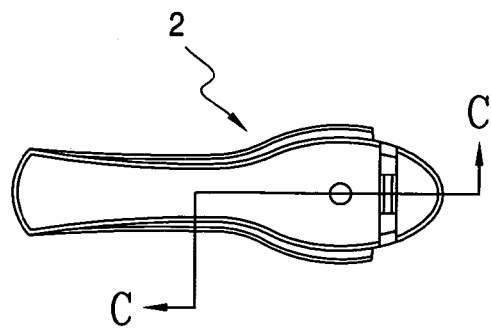
FIGS. 1A, 1B and 1C are respective side view, top view and sectional view of an exemplar combination cannula/trocar device.
Figure 1A:
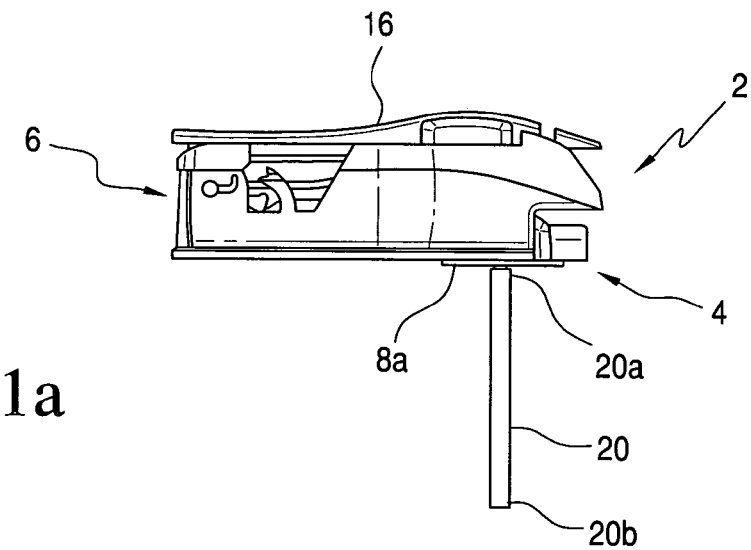
Figure 1C:
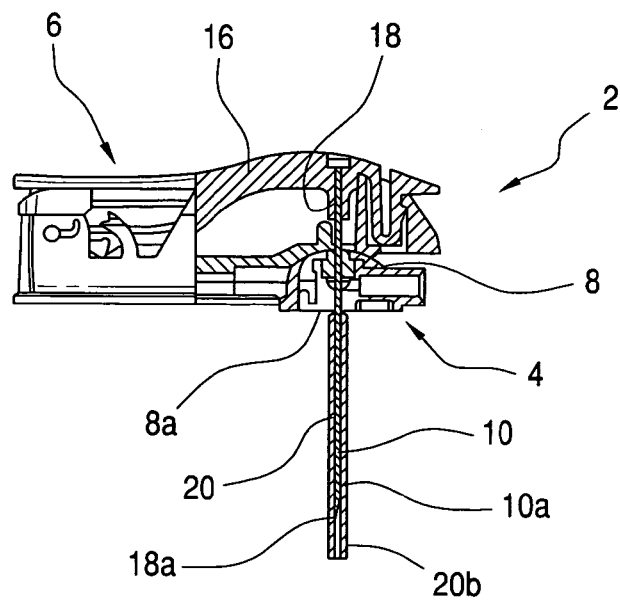

With reference to FIGS. 1A-1C, an exemplar cannula/trocar device 2 of the invention disclosed in publication 2007/0149921 and 2007/0149920 is shown. FIG. 1A shows the side view of the device, FIG. 1B shows the top view of the device and FIG. 1C shows a cross-sectional view of the device. The respective disclosures of the '921 and '920 publications are incorporated by reference herein.

As shown, device 2 has an infuser or an infusion site 4 and an inserter or inserter assembly 6. As best shown in FIG. 1C, the infusion site has a base or a septum 8 that is fitted to a concave space in inserter assembly 6. Also with reference to FIGS. 2 and 3, a cannula 10 that may be made of stainless steel extends from the bottom surface 8a of base 8. For this discussion, bottom surface 8a is assumed to be a part of the base even though in actuality it may be the bottom surface of a foam pad 12 having an adhesive layer for making contact with the patient. A tube 14, as shown in FIG. 3, is attached to septum 8 for providing a fluid thereinto.

Figure 2:
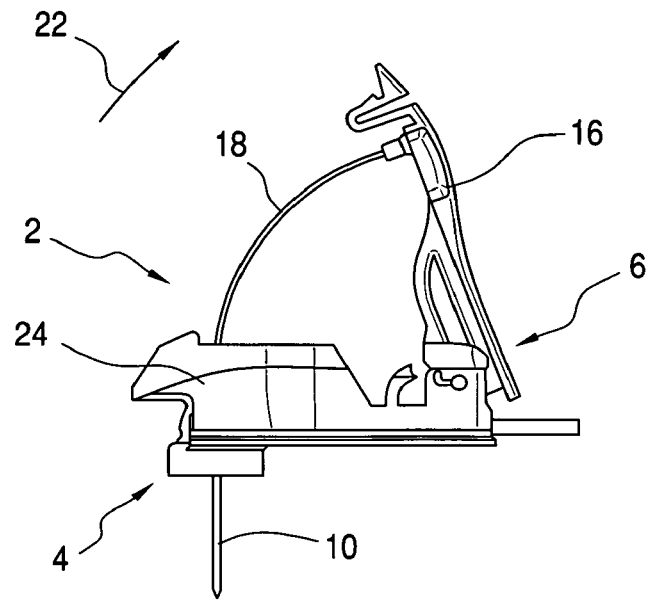
FIG. 2 is a side view of the exemplar combination cannula/trocar device shown in FIG. 1A.
Figure 3:
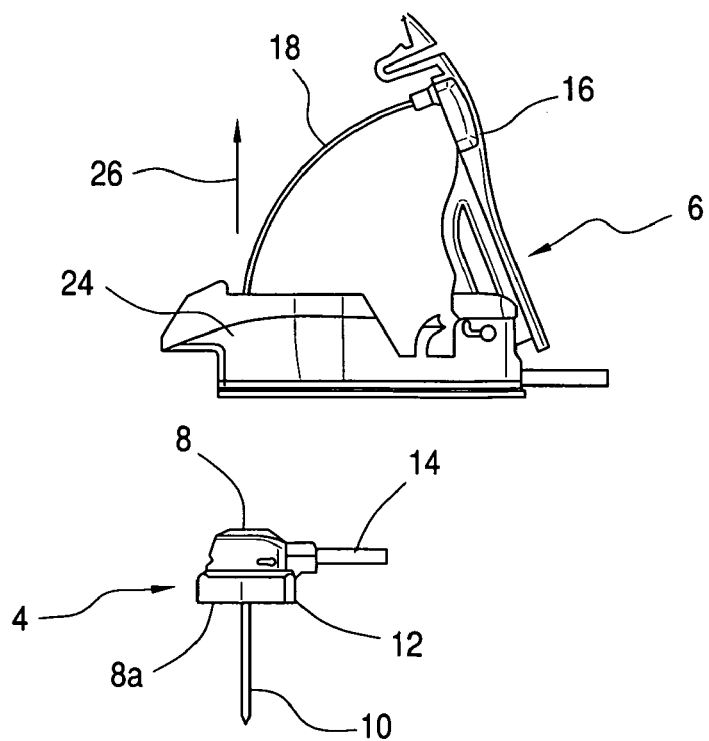
FIG. 3 is a side view of the FIG. 1A device having its infusion site removed from its insertion assembly.

Returning to the device shown in FIGS. 1A-1C, prior to the use, the infusion site 4 is mated to inserter assembly 6, which has a handle 16 that has connected thereto a needle or trocar 18, best shown in FIGS. 2 and 3. Trocar 18 is shown to be inserted through cannula 10 so that its tip 18a extends beyond the distal end 10a of cannula 10. For the device shown in FIGS. 1A-1C, a tube protector 20 having a proximal end 20a and a distal end 20b is fitted about cannula 10, with its proximal end 20a in substantial abutment against the bottom surface 8a of base 8 of infusion site 4. As best shown in FIG. 1C, the distal end 20b of tube 20 extends beyond both the tip 18a of trocar 18 and the distal end 10a of cannula 10. Accordingly, tube 20 acts as a protector for cannula 10 as well as trocar 18. Putting it in another light, tube 20 protects a user from tip 18a of trocar 18, and also maintains the sterilization of cannula 10 and trocar 18 prior to use.

For the device 2 shown in FIG. 1C, note that the inner diameter surface (ID) of tube 20 is in a line to line contact with the outer diameter surface (OD) of cannula 10, so that there is friction contact between tube 20 and cannula 10 along their respective inner and outer diameter surfaces. Also note that there is a line to line contact between the inner diameter surface (ID) of cannula 10 and the outer diameter surface (OD) of trocar 18.

For the device 2 shown in FIG. 1, trocar 18 and cannula 10 are both manufactured from stainless steel while tube 20 is manufactured from plastic, in particular an extruded tubing made for example from polyethylene. As such, the manufacture tolerances for the cannula and trocar are required to be higher than the manufacture tolerance for the tubing. For example, a reasonable tolerance for an extruded polyethylene tubing may be +/−0.002 inch on the inner diameter (ID) of the extruded tubing. Being made from stainless steel, the manufacture tolerance for the trocar and the cannula is less varied, and may be assumed to be constant for the discussion of the instant invention.

As shown in FIGS. 2 and 3, the inserter assembly 6 is removable from the infusion site 4, when trocar 18 is moved out of cannula 10, per shown by the pivotal movement of handle 16, designated by directional arrow 22 in FIG. 2, relative to the main body 24 of the inserter assembly 6. Once trocar 18 is removed from cannula 10, inserter assembly 6 may be removed from infusion site 4, per shown by an upward movement indicated by directional arrow 24 in FIG. 3.

The problem of using tube 20 for enclosing cannula 10 and trocar 18 is that the friction contact between the inner diameter surface of tube 20 and the outer diameter surface of cannula 10 may create a static friction that may in turn effect a vacuum suction that causes cannula 10 and tube 20 to move in unison or tandem, when a user tries to remove tube 20 from cannula 10, so as to use device 2. Putting it differently, the friction contact between tube 20 and cannula 10 is greater than the friction contact between cannula 10 and trocar 18. As a result, the force that is required to remove tube 20 from cannula 10 is greater than the force that is required to separate cannula 10 from trocar 18.

The tube protector of the instant invention overcomes the shortcoming of tube 20.

Figure 4B:
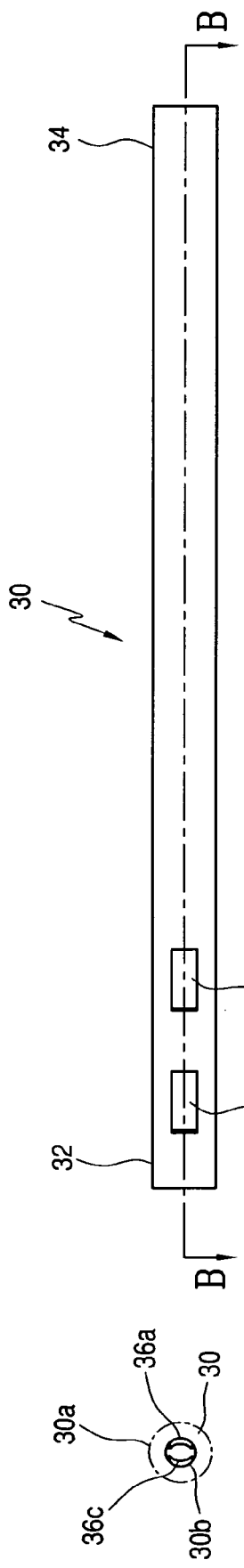
FIG. 4B is a cross-sectional view of the tube protector of the instant invention at view B-B.
Figure 4A:
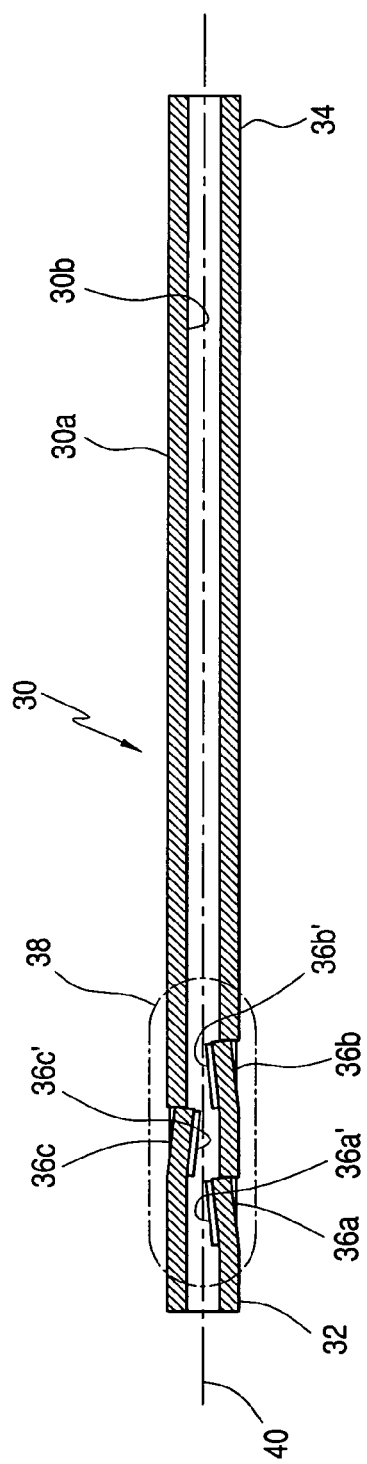
FIG. 4A is a side view of the tube protector of the instant invention.
Figure 4C:
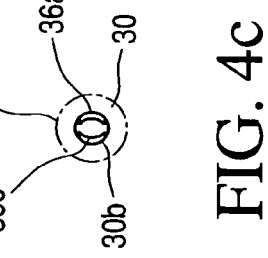
FIG. 4C is an end view of the tube protector of the instant invention.

With reference to FIGS. 4A, 4B and 4C, a tube protector 30 of the instant invention is illustrated. For the discussion of tube protector 30, except for tube 20, the components disclosed in FIGS. 1-3 remain the same and accordingly are labeled the same in FIG. 4. As shown, tube 30 is manufactured from plastic and may be an extruded polyethylene tubing. Tube 30 has an outer circumferential wall or outer diameter surface 30a and an inner circumferential wall or inner diameter surface 30b, and has a proximal end 32 and a distal end 34. As best shown in FIGS. 4A and 4B, a plurality of protrusions 36a, 36b and 36c are provided at a section 38 of tube 30. These protrusions may also be referred to as protuberances or dimples. Although shown to be proximate to proximal end 32, section 38 may be located anywhere along the length of tube 30. For the instant invention embodiment, tube 30 is to be fitted about cannula 10, with its proximal end 32 in abutment against bottom surface 8a of the infusion site 4 and its distal end 34 extending beyond and therefore covering both the tip 18a of trocar 18 and the distal end 10a of cannula 10, per shown in FIG. 1C, assuming that tube 20 has been removed therefrom, and per shown more clearly in FIG. 5.

Returning to FIGS. 4A and 4B, note that protrusion 36c is located 180° or opposed to, and between protrusions 36a and 36b. In other words, to be more effective in the inventive tube protector 30, one of the plurality of protrusions is positioned directly opposed to and below and above the respective other protrusions, if there are to be three protrusions effected at section 38. These protrusions may be punched or lanced by the punch shown in FIG. 6 so that the protrusions would extend inwardly toward the center interior of tube 30, as exemplified by its longitudinal axis 40. Although a greater or smaller number of protrusions may be used, it was found that with the center protrusion 36c and its two 180° opposed upper and lower protrusions 36a and 36b, an effective friction fit arrangement is obtained that provides a slight bend for tube 30 at section 38, when tube 30 is fitted about a straight cannula such as for example cannula 10, or a trocar such as for example trocar 18, so that tube 30 will stay put once fitted about a cannula or trocar.

FIG. 4C shows an end view of tube 30, from proximal end 32. Note that each of the protrusions 36 has a tip or distal portion (designated 36a', 36b' and 36c') extending inwardly towards the interior of tube 30.

Figure 5:
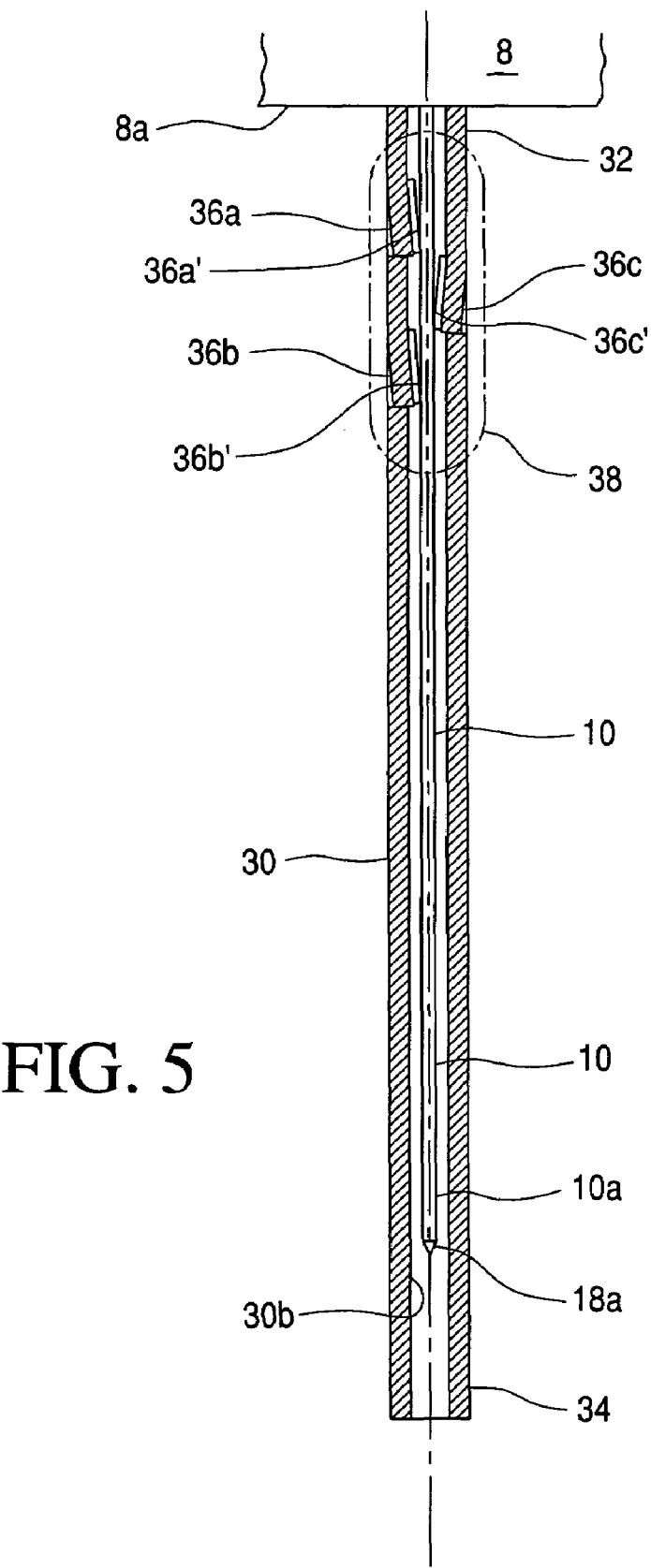
FIG. 5 is a cross-sectional view showing the tube protector of the instant invention fitted about a combination cannula/trocar.

With reference to FIG. 5, tube protector 30 is shown to be fitted about cannula 10 that in turn has fitted therethrough trocar 18, with trocar tip 18a shown extending out beyond the distal end 10a of cannula 10. For the FIG. 5 embodiment, tube 30 is shown to be fitted about cannula 10 by its proximal end 32 being in abutment with bottom surface 8a of base 8 of the infusion site 4. Thus, section 38 of tube 30 is located at the upper end of cannula 10, with the plurality of protrusions 36 and more particular their respective tips 36a', 36b' and 36c', in contact with the outer diameter surface of cannula 10. As such, friction contact that prevents free movement between tube 30 and cannula 10 is provided, so that tube 30 is held in place relative to cannula 10.

The protrusions 36 may be punched or lanced into tube 30 to a given depth to generate a particular friction contact between tube 30 and cannula 10 to specify the force that is required to remove or separate tube 30 from cannula 10. Thus, the force required to separate tube 30 from cannula 10 can be specified to be less than the force that is required to remove or separate cannula 10 from trocar 18. For the instant invention, it was found that the force required to separate tube 30 from cannula 10 is approximately 0.25 lb., whereas the force that is required to separate cannula 10 and trocar 18 (which are in a line to line friction contact) is approximately 2.50 lb. Thus, approximately 10 times more force is needed to separate cannula 10 from trocar 18 than to separate tube 30 from cannula 10. As a result, when a user applies a predetermined force, such as for example the noted 0.25 lb. to remove tube 30 from cannula 10, cannula 10 would remain in position relative to trocar 18, as the friction contact provided by the line to line contact between the inner diameter surface of cannula 10 and the outer diameter surface of trocar 18 is greater than the friction contact between the protrusions 36 of tube 30 and the outer diameter surface of cannula 10.

Thus, by upsetting the inside diameter surface of tube 30 by lancing protrusions 36 thereat, a predefined friction contact may be provided between tube 30 and cannula 10, due to the protrusions 36 coming into contact with the outer diameter surface of cannula 10. The fact that the protrusions 36 are controllably punched at a predefined depth into tube 30 also cause tube 30 to bend slightly at section 38 to enhance the friction contact, when tube 30 is placed onto or fitted about the straight cannula 10 and trocar 18.

An additional advantage with lancing the protrusions 36 at tube 30 is that a tactile feel is provided to the user when tube 30 is being separated or removed from cannula 10. This results from the fact that so long as section 38 of tube 30 covers cannula 10, each of the protrusions 30 would bias against the outer diameter surface of cannula 10. But as soon as one of the protrusions 36 no longer is in contact with cannula 10, it tends to spring further inwardly towards the interior of tube 30, thereby providing the user who presumably is holding tube 30 a tactile feel reflecting that a portion of the biasing force has receded.

The fact that section 38 is positioned proximate to proximal end 32 of tube 30 means that there is a longer distance for the protrusioned section 38 to travel along the length of cannula 10, thereby ensuring that the respective distal end 10a of cannula 10 and tip 18a of trocar 18 be protected, even in the event that tube 30 was accidentally pulled partially downwards away from bottom surface 8a of infusion site 8.

Although tube 30 is disclosed in FIG. 5 to protect a combination cannula/trocar device, it should be appreciated that the tube protector of the instant invention may be used with only a cannula, or a trocar. With the protrusioned or dimpled tube protector, the manufacturing cost for such is reduced, as the relatively larger variance in the manufacture of the tube diameter can be tolerated. Moreover, the protrusioned tube protector gives the user a tactile feel, when the protector is removed from either the cannula or the trocar.

Figure 6:
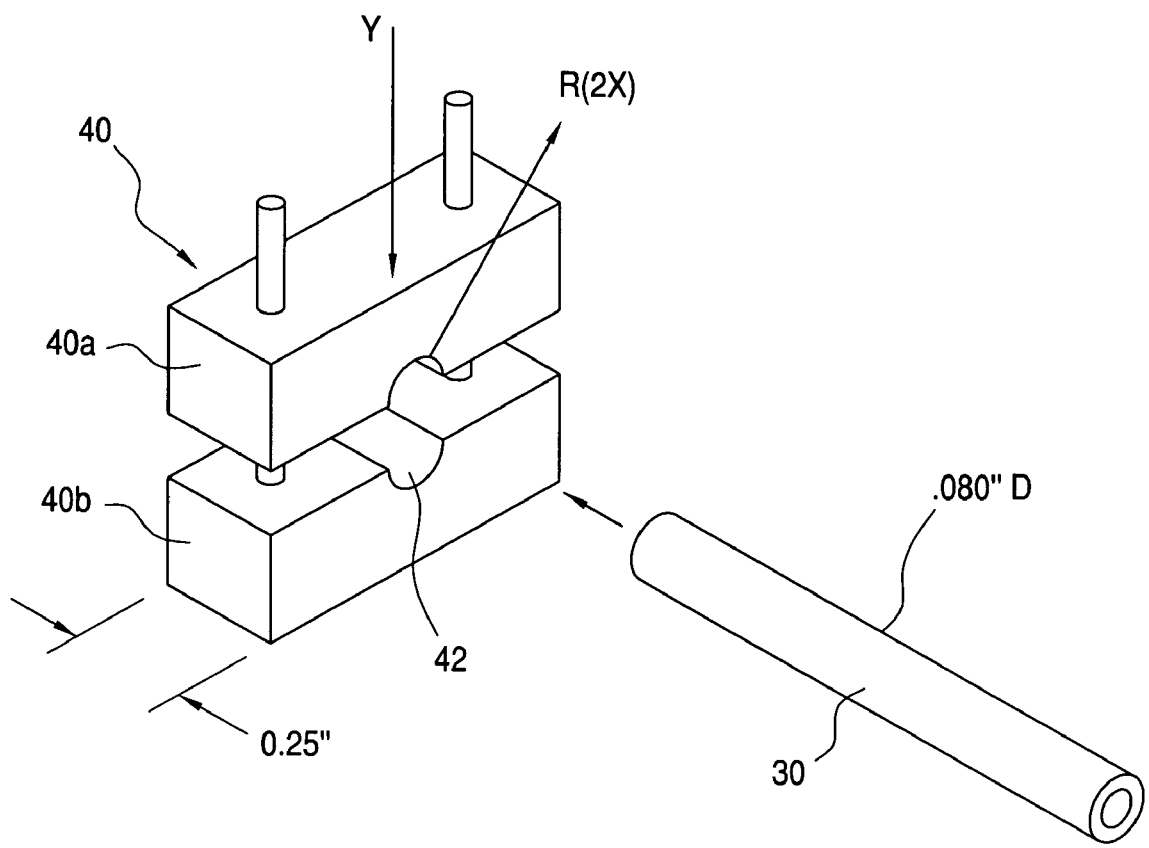
FIG. 6 is a perspective view of a punch that may be used to manufacture the tube protector of the instant invention from an extruded tubing.

FIG. 6 shows an exemplar punch 40 used to effect protrusions on an extruded tubing having an exemplar 0.080 inch diameter. As shown, tube 30 is inserted into punch 40 through an opening 42 a given distance, for example 0.25 inch as illustrated. Once fully inserted, top punch 40a presses downward onto die 40b so that the punches for the protrusions (not shown) inside die 40 can lance or punch the protrusions onto that section of tube 30. As the operation of punch 40 can be carefully controlled and the punch depth of the punches adjustable, the depth of the plurality of protrusions punched in tube 30 can be predetermined to obtain a predefined friction contact when the protrusions come into contact with the cannula and/or trocar. This means that amount of force required to separate the tube from the cannula and/or trocar can be selectively calculated.

Instead of the three protrusions arrangement disclosed, depending on the materials of the tubular/trocar as well as the tube, only one protrusion may be all that is needed to effect an effective friction contact between the tube protector and the cannula, trocar, or cannula/trocar combination to ensure that the tube protector is separable from the cannula/trocar as discussed above. Conversely, a plurality of more than three protrusions may also be used.

Although at least one protrusion or opposed protrusions punched into the tube protector are disclosed as being used to effect a friction contact between the tube and the cannula/trocar, it should be appreciated that other means for effecting friction contact between the tube and the cannula/trocar may also be used. For example, instead of protrusions or dimples, a section of the tube protector may be crimped so that an internal groove may be formed at a given section of the tube to come into contact with the outer diameter surface of the cannula/trocar for effecting the friction fit. Instead of one internal groove, additional internal grooves may be used. Instead of a circumferential internal groove, the groove may be intermittent, or intermittently staggered as for example similar to the relationship illustrated by the protrusions shown in FIGS. 4 and 5.

The invention claimed is:

1. A protector for a cannula having a base and a tip, comprising: an elongate tube having a length to enable it to fit about said cannula and extend from the base of said cannula to beyond the tip of said cannula, said cannula having an outer diameter surface, said tube having an inner diameter surface not in contact with the outer diameter surface of said cannula when fitted about said cannula, said tube including at least three protrusions formed at a given section of said tube with each of said protrusions extending inwardly toward the center of said tube, wherein said protrusions each are dimensioned inwardly toward the center of said tube to come into contact with the outer diameter surface of said cannula when said tube is fitted about said cannula so that said tube is held in place relative to said cannula by friction contact between said protrusions and the outer diameter surface of said cannula, wherein one of said protrusions is positioned at said tube directly opposed to, and below and above respective ones of the other two protrusions to provide a slight bend at said given section to enhance the friction contact with said cannula when said tube is fitted about said cannula, said tube separable from said cannula when a predetermined force is applied to remove said tube from said cannula.

2. Protector of claim 1, wherein said protrusions each are produced by said tube being punched from its outside surface to effect a protuberance that protrudes into the interior of said tube.

3. Protector of claim 1, wherein said protrusions are located proximate to the end of said tube that fits toward the base of said cannula.

4. Protector of claim 1, wherein said cannula is fitted about a trocar and held in place with said trocar by friction contact between its inner diameter surface and the outer diameter surface of said trocar, wherein the force required to overcome the friction contact between said cannula and said trocar is greater than the force required to overcome the friction contact between said protrusions of said tube and said cannula.

5. Protector of claim 1, wherein said cannula is made of stainless steel and said tube is made of plastic.

6. In combination, an infusion site having a base with a bottom surface and a cannula having a distal end extending from the bottom surface of said base, a trocar having an outer diameter surface and a tip extending through said base into said cannula with its tip extending beyond the distal end of said cannula, and a tube separate from said trocar having a distal end and a proximal end fitted about said cannula with the distal end of said tube extending beyond the tip of said trocar and the distal end of said cannula when the proximal end of said tube is in substantial abutment with the bottom surface of said base to prevent the tip of said trocar from being exposed, said cannula having an inner diameter surface and an outer diameter surface, said cannula being held to said trocar by friction contact between the inner diameter surface of said cannula and the outer diameter surface of said trocar, wherein said tube comprises an inner diameter that is sufficiently greater than the outer diameter of said cannula such that said tube would be freely movable relative to said cannula when fitted about said cannula, and wherein said tube includes at least one protrusion extending inwardly towards the interior of said tube, said protrusion coming into contact with the outer diameter surface of said cannula to establish friction contact with said cannula when said tube is fitted about said cannula such that said tube is prevented from being separated from said cannula without a predetermined force being exerted to remove said tube from said cannula, said tube being separated from said cannula when said predetermined force is exerted to remove said tube from said cannula, said cannula and said trocar continued to be held together while said tube is being separated from said cannula due to the exertion of said predetermined force as the force required to overcome the friction contact between the inner diameter surface of said cannula and the outer surface of said trocar is greater than said predetermined force.

7. Combination of claim 6, wherein there are at least three protrusions at said tube, with one protrusion being directly opposed to, and below and above respective ones of the other two protrusions.

8. Combination of claim 6, wherein the friction contact between said cannula and said trocar is greater than the friction contact between said protrusion at said tube and said cannula, and wherein the predetermined force sufficient to separate said tube from said cannula is not enough to separate said cannula from said trocar.

9. Combination of claim 6, wherein said cannula and said trocar each are made of stainless steel and said tube is made of plastic.

10. A protector for a cannula having a distal end and having fitted therethrough a trocar, said trocar having a tip that extends beyond the distal end of said cannula, said cannula and said trocar being in friction contact with each other along their respective outer diameter surface and inner diameter surface, said protector comprising: a tube separate from said trocar having a length longer than either one of said trocar and cannula so that the tip of said trocar is covered by a distal end of said tube when said tube is fully fitted over said cannula, said tube having an inner diameter greater than the outer diameter of said cannula so that said tube is freely movable relative to said cannula when fitted about said cannula, said tube further having at least one protrusion extending into its interior, said protrusion being in contact with the outer wall surface of said cannula when said tube is fitted about said cannula to establish friction contact with said cannula so that a predetermined force is required to be applied to said tube in order to separate said tube from said cannula, wherein said tube is removed from said cannula when said predetermined force is applied to said tube, said cannula and said trocar continued to be in friction contact with each other as said tube is removed from said cannula as the force required to overcome the friction contact between said cannula and said trocar is greater than said predetermined force.

11. Protector of claim 10, wherein there are at least three protrusions at said tube, with one protrusion being directly opposed to, and below and above respective ones of the other two protrusions.

12. Protector of claim 10, wherein said cannula and said trocar each are made of stainless steel and said tube is made of plastic.

13. A method of making a protector for a cannula having a first diameter, comprising the steps of:
    extruding a tube having a second diameter that is larger than the first diameter of said cannula so that said tube is freely movable along said cannula if said tube is fitted about said cannula; and
    effecting at least three protrusions at a given section of said tube with said protrusions extending into the interior of said tube, wherein one of said protrusions is positioned directly opposed to, and below and above respective ones of the other two of said protrusions to provide a slight bend at said given section to enhance the friction contact with said cannula when said tube is fitted about said cannula, said protrusions being in friction contact with the outer surface of said cannula when said tube is fitted about said cannula so that said tube is removable from said cannula only if a predetermined force is exerted to separate said tube from said cannula.

14. Method of claim 13, wherein said effecting step comprises the step of punching said protrusions in said tube to ensure that the friction contact between said protrusions and said cannula is less than the friction contact between a trocar inserted in said cannula and said cannula so that the removal of said tube from said cannula does not cause said cannula to be separated from said trocar.

\* \* \* \* \*